United States Patent
Beisel

(10) Patent No.: US 6,541,031 B1
(45) Date of Patent: Apr. 1, 2003

(54) COMPOSITION WITH RELEASE-CONTROLLING ACTION

(76) Inventor: Günther Beisel, Schloss Laach, D-40789 Monheim (DE)

( * ) Notice: Subject to any disclaimer, the term of this patent is extended or adjusted under 35 U.S.C. 154(b) by 0 days.

(21) Appl. No.: 09/356,391

(22) Filed: Jul. 16, 1999

Related U.S. Application Data

(63) Continuation of application No. PCT/EP96/03950, filed on Sep. 7, 1996.

(51) Int. Cl.⁷ ............... A61K 9/10; A61K 9/12; A61K 9/70; A61K 9/48; A61K 47/42
(52) U.S. Cl. ............ 424/484; 424/400; 424/452; 424/443; 514/773
(58) Field of Search ............... 424/486, 484, 424/452, 443, 400; 514/773

(56) References Cited

U.S. PATENT DOCUMENTS

| | | |
|---|---|---|
| 3,435,110 A | 3/1969 | Nichols |
| 5,603,950 A | 2/1997 | Ratjen et al. |
| 5,643,596 A * | 7/1997 | Pruss et al. |
| 5,651,985 A | 7/1997 | Penners et al. |

FOREIGN PATENT DOCUMENTS

| | | |
|---|---|---|
| DE | 4419818 | 12/1995 |
| EP | 0170979 | 12/1986 |
| WO | 9117745 | 11/1991 |

* cited by examiner

Primary Examiner—Edward J. Webman
(74) Attorney, Agent, or Firm—Friedrich Kueffner

(57) ABSTRACT

The present invention relates to a composition for delayed and gentle release of active substances (4) in the body, containing a carrier material which is insoluble or of low solubility in water and gastrointestinal fluids or other body fluids, active substances (4) and, where appropriate, other ancillary substances and, where appropriate, a coating which is soluble in water and gastrointestinal fluids or other body fluids, wherein the composition is obtainable by compressing to various shapes a sponge-like structure (1, 2) of the carrier material which is loaded with active substances (4) and, where appropriate, providing it with a coating.

13 Claims, 1 Drawing Sheet

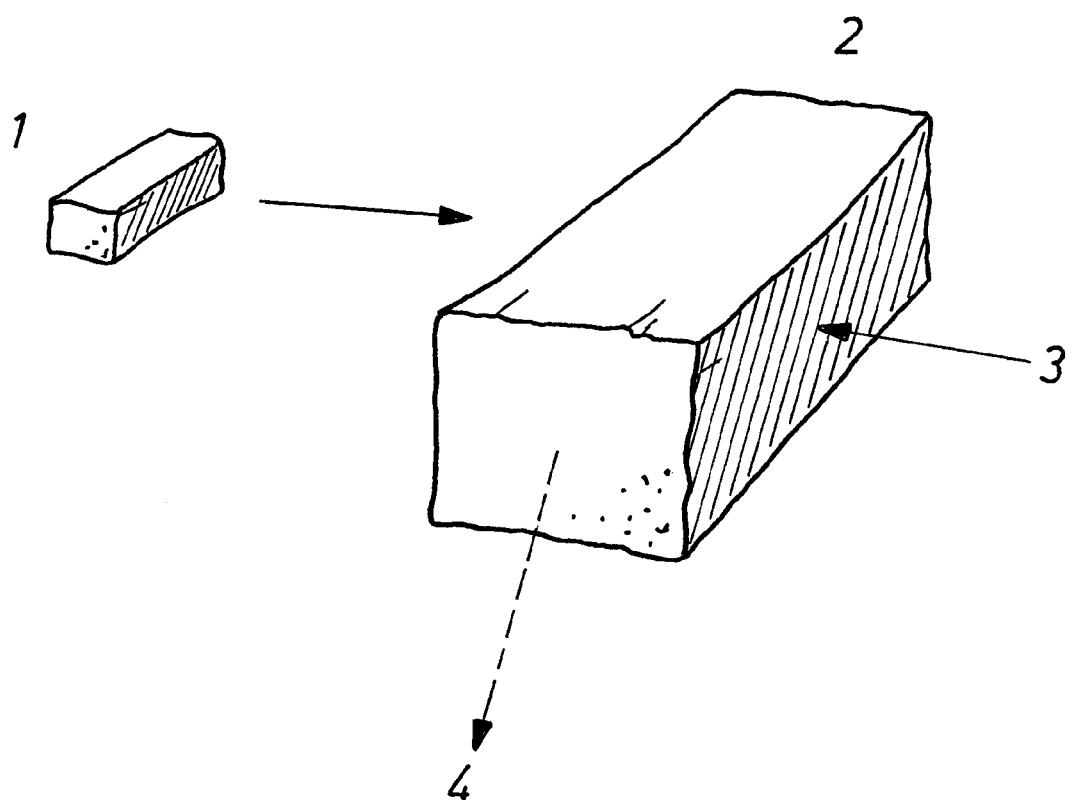

COMPOSITION WITH RELEASE-CONTROLLING ACTION

This application is a Continuation Application of International Application Ser. No. PCT/EP96/03950 filed Sep. 7, 1996.

BACKGROUND OF THE INVENTION

The present invention relates to a further development in the area of active substance systems with delayed and gentle release of active substances from a carrier material, in particular from the sector of medical and/or biological products. Combination materials of this type, in particular from the sector both of pharmaceutical ancillary substances and biological preparations, for example crop protection agents, are the subject of numerous investigations and printed publications. They are referred to, for example, by the terms controlled release systems, depot or slow release materials or, very generally, as compositions with delayed release of product.

DESCRIPTION OF THE RELATED ART

The release-controlling action can be brought about for example, by a coating process in which granules or a tablet which has already been shaped is coated with an enveloping layer through which the active substance diffuses over a lengthy period (compare, for example, DE-A 4239244). In order to achieve release of active substance which is controlled as possible, U.S. Pat. No. 3,916,899 describes, for example, a release-controlling form for active substances in which the active substance reservoir is surrounded by a semipermeable coating layer which is impermeable to the active substance but permeable to the particular liquid in the surrounding medium. The surrounding coating layer additionally contains a geometrically well-defined orifice through which the active substance, which is dissolved in the surrounding liquid, can reach the outside. After the composition is taken, the digestive fluids diffuse through the semipermeable coating layer into the interior of the capsule. The active substance in the interior of the capsule is continuously dissolved in the in flowing liquid and reaches the outside through the geometric orifice in the coating layer at a defined rate.

However, with this system there is repeatedly local irritation of the tissue in the gastric or intestinal tract, depending on the capsule contents employed, due to elevated concentrations. In addition, part of the active substance as a rule remains in the medicinal form and is thus not available for the desired absorption. In addition, the production of the release-controlling form is very elaborate because the coating layer must be provided with the defined orifices.

In another process, the depot materials consist of a carrier with or without its own action, into which the product which is to undergo delayed release is incorporated. Particular attention has been paid in the literature in recent years to polymeric compounds based on polyesters from lower hydroxy carboxylic acids with, in particular 2–6 C atoms in the hydroxy carboxylic acid molecule as carrier material. Carrier materials of this type are in turn labile to hydrolysis and subject to biological mechanisms.

From the recent relevant literature, reference may be made, for example, to U.S. Pat. No. 4,011,312 which discloses solid formulations of copolyesters of glycolic acid and lactic acid with molecular weights below 2,000 as carrier material mixed with antibiotic active substances such as tetracycline, neomycin and other antibiotics. Numerous investigations deal with the use of absorbable polyesters based on glycolic acid/lactic acid as carrier material with delayed release of active substance (compare, for example, D. L. Wiese et al. in: Drugs Carriers in Medicine Academic Press London 1979, pages 237–270).

A specific manner of controlling release by means of carrier-bound active substances is disclosed in DE-A 4413350. This describes a controlled release form in which the active substance is embedded in a mixture of a water-insoluble polymer, a lipid and a polymer which is soluble in water to form a highly viscous colloid, forms a gel or is at least able to swell in water. The basic principle of the polymer matrix described therein is a matrix which is classified by suitable lipophilic substances and consists of a polymer which is insoluble in water and gastrointestinal fluids. Additionally incorporated into this matrix of insoluble polymer and lipophilic component is a gel former, that is to say a polymer which forms a highly viscous solution, or is at least able to swell, in water. This gel former brings about breaking open of the release-controlling matrix by the swelling on contact with gastric fluid, so that the active substance can be released.

A disadvantage of this design of a controlled release form is the very complicated mode of production, in particular the matching of the various components responsible for the release-controlling action. An additional factor is that all the controlled release forms hitherto described reach the stomach in the form of small-volume structures and, as a rule, their volume does not increase considerably there either. The medicinal compositions may therefore be deposited in folds of the intestine and the stomach. The consequence may be irritation or even perforation of the gastric and intestinal walls. In addition, with the small-volume medicines hitherto, there is not the required uniform distribution of the delayed released active substances in the gastrointestinal tract.

SUMMARY OF THE INVENTION

It is accordingly an object of the present invention to provide a composition with delayed and gentle release of the active substances, containing a swelling carrier material which is insoluble, or soluble after a delay, in water and gastrointestinal fluids, active substances and where appropriate, conventional ancillary substances and, where appropriate, a coating which is soluble in water and gastrointestinal fluids, which does not have the disadvantages described for controlled release forms hitherto. In particular, the intention is that the composition prevent, by its large-volume form, local irritation occurring due to deposition on the walls of the stomach and intestine. In addition, the intention is to achieve distribution of the released active substances over an area as large as possible in the gastrointestinal tract.

This object is achieved by a composition which is obtainable by a large-volume, sponge-like structure of a carrier material which is loaded with active substance being partly compressed to various shapes and, where appropriate, being provided with the coating.

Sponge-like structures mean according to the invention foams which consist of gas-filled spherical/polyhedral cells which are limited by highly viscous or solid cell walls. It is possible to employ according to the invention both naturally occurring sponges and synthetically produced sponge-like structures.

The sponge-like structures are produced by methods known per se from the state of the art. Depending on the starting material employed, in the simplest case a foam can be obtained by blowing in, by beating, shaking, spraying or stirring in the relevant gas atmosphere. In the case of polymers, the foam structure arises due to chemical reactions. Thus, polyurethanes are foamed by adding blowing agents which decompose at a particular temperature during the processing to form a gas, or by adding liquid solvents during the polymerization. The foaming takes place either on leaving the extrusion die, that is to say following the extrusion or injection moulding or in open moulds. Curing takes place under the conditions characteristic of the particular chemical compound of the carrier material.

An indispensable prerequisite for the employability of the carrier material according to the invention and of the sponge structure is that the material can be compressed without the cell walls breaking. This is because in order to be able to employ the carrier material according to the invention for a composition, the foam-like carrier material must be compressed to a size which is suitable for oral or enteral administration. The carrier material is normally compressed to a volume not exceeding 2 cm$^3$. For usual dosage forms the volume should be below 3 cm$^3$.

The compression consists of the carrier material being pressed or compressed in a similar manner, whereby it is reduced to a fraction of its free volume. The carrier material is for this purpose expediently cut to its final size beforehand. If the composition according to the invention is to be administered in the form of capsules, the pressed block produced in this way can be sealed in a capsule.

It is likewise possible for the pressed block to be coated with a coating layer or other protective layers, which dissolves only under the influence of gastrointestinal fluid.

Finally, it is also essential for the selection of the carrier material and the manner of foam formation that the material remains swellable without the cell walls being destroyed. Under physiological conditions, the compressed carrier material should preferably be able to expand its volume by two- to ten-fold, particularly preferably by four- to eight-fold.

The active substance release areas of the carrier material which has enlarged under physiological conditions are, according to the invention, 15 to 25 cm$^2$. By comparison therewith, the figures for the release areas according to the state of the art are 0.5 to 1.5 cm$^2$.

It is possible to employ as carrier material according to the invention natural, semisynthetic or synthetic polymers. Examples of suitable synthetic polymers are polyurethanes, polyacrylates, poly(meth)acrylic esters, homo- and copolymers of vinyl acetate. The natural and semisynthetic polymers include cellulose, ethers, diethylcellulose or cellulose esters, such as cellulose diacetate, cellulose triacetate, cellulose acetate propionate and cellulose acetate butyrate. Examples which are suitable according to the invention are cellulose derivatives, especially corresponding ethers, for example methylcellulose, hydroxypropylcellulose, hydroxypropylmethylcellulose or sodium carboxymethylcellulose (preferably those compounds with relatively high viscosity); certain polymers such as polyacrylic acid and salts thereof; natural (anionic) mucilages, for example xanthan gum, guar gum, tragacanth or alginic acid and salts thereof, and the like. Furthermore, the use of insoluble polysaccharides such as chitin or chitin derivatives or microcrystalline cellulose is also conceivable. Particularly preferred according to the invention are linear higher molecular weight polymers. It is particularly possible to employ according to the invention those polymers which have a fibrous structure. Examples of such substances are the scleroproteins such as keratins, conchagens, fibrin, elastins, chitin and collagen. The latter is particularly preferred according to the invention.

The compression is expediently preceded by the loading with active substances. This can take place before, during or after the production of the sponge-like structure. All conventional methods are suitable for the loading with active substance. In the simplest case, this can take place during the production of the sponge material by mixing carrier material and active substance. This is followed by drying and carrying out the compression described.

The amount of active substance per dose unit and the concentration may vary within wide limits depending on the activity and required release rate. The only condition is that they suffice to achieve the required effect and aim. Thus, the concentration of active substance can be in the range from 0.1 to 87, preferably 1 to 80, in particular 1–75% by weight.

Active substances for the purpose of the invention are all substances with a pharmaceutical or biological action. Examples are betamethasone, thioctic acid, sotalol, salbutamol, norfenefrine, silymarin, dihydroergotamine, buflumedil, etofibrate, indometacin, oxazepam, beta-acetydigoxin, piroxicam, haloperidol, ISMN, amitriptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(beta-hydroxyethyl)rutoside, propicillin, aciclovir mononitrate, paracetamol, naftidrofuryl, pentoxyfylline, propafenone, acebutolol, L-thyroxine, tramadol, bromo-criptine loperamide, ketotifen, fenoterol, Ca-dobelisate, propranolol, minocycline, nicergoline, ambroxol, metoprolol, beta-sitosterol, enalapril maleate, bezafibrate, ISDN, gallopamil, xanthinol nicotinate, disitoxin, flunitrazepam, bencyclane, dexpanthenol, pindolol, lorazepam, diltiazem, piracetam, phenoxymethyl-penicillin, furosemide, bromazepam, flunarizine, erythromycin, metoclopramide, acemetacin, ranitidine, biperiden, metamizole, doxepine, dipotassium chloroazepate, tetrazepam, estramustine phosphate, terbutaline, captopril, maprotiline, prazosin, atenolol, glibenclamide, cefaclor, etilefrine, cimetidine, theophylline, hydromorphone, ibuprofen, primidone, clobazam, oxaceprol, medroxyprogesterone, flecainide, Mg pyridoxal-5-phosphate glutamate, hymechromone, etofylline clofibrate, vincamine, cinnarizine, diazepam, ketoprofen, flupentixol, molsidomine, glibornuride, dimethindene, melperone, soquinolol, dihydrocodeine, clomethiazole, clemastine, glisoxepide, callidinogenase, oxyfedrine, baclofen, carboxymethylcysteine, thioridazine, beta-histine, L-tryptophan, myrtol, bromelains, prenylamine, salazosulfapyridine, astemizole, sulpiride, benserazide, dibenzepine, acetylsalicylic acid, miconazole, nystatin, ketoconazole, Na picosulphate, colestyramine, gemifibrozil, rifampicin, fluorocortolone, mexiletine, amoxicillin, terfenadrine, mucopolysaccharide poly-sulphates, triazolam, mianserin, tiaprofenic acid, amezinium metilsulphate, mefloquine, probucol, quinidine, carbamazepine, Mg L-aspartate, penbutolol, piretanide, amitriptyline, cyproterone, Na valproate, mebeverine, bisacodyl, 5-aminosalicylic acid, dihydralazine, magaldrate, phenprocoumon, amantadine, naproxen, carteolol, famotidine, methyldopa, auranofin, estriol, nadolol, levomepromazine, doxorubicin, meclofenoxate, azathioprine, flutamide, norfloxacin, fendiline, prajmalium bitartrate, aescin.

Further examples are the following active substances: acetaminophen (=paracetamol), acetohexamide, acetyldigoxin, acetylsalicylic acid, acromycin, anipamil, benzocaine, beta-carotene, choramphenicol, chlordiazepoxide, chlormadinone acetate, chlorothiazide, cinnarizine, clonazepam, codeine, dexamethasone, diazepam, dicumarol, digitoxin, digoxin, dihydroergotamine, drotaverine, flunitrazepam, furosemide, gramicidin, griseofulvin, hexobarbital, hydrochlorothiazide, hydrocortisone, hydroflumethiazide, indomethacin, ketoprofen, lonetil, medazepam, mefruside, methandrostenolone, methylprednisolone, methylsulfadiazine (=sulfaperin), nalidixic acid, nifedipine, nitrazepam, nitrofurantoin, nystatin, oestradiol, papaverine, phenacetin, phenobarbital, phenylbutazone, phenytoin, prednisone, reserpine, spironolactone, streptomycin, sulfadimidine (=sulfamethazine), sulfamethizole, sulfamethoxazole (=sulfameter), sulfaperin, sulfathiazole, sulfisoxazole, testosterone, tolazamide, tolbutamide, trimethoprim, tyrothricin, vitamins, minerals.

Besides the active substances mentioned, it is also possible to add other ancillary substances to the carrier material. Inter alia, release-controlling substances may also be suitable in addition.

Release-controlling ancillary substances which can be used are essentially water-insoluble ancillary substances or mixtures thereof, such as lipids, including fatty alcohols, for example cetyl alcohol, stearyl alcohol and cetostearyl alcohol; glycerides, for example glycerol monostearate or mixtures of -mono-, di- and triglyderides, vegetable oils; hydrogenated oils such as hydrogenated castor oil or hydrogenated cotton seed oil; waxes, for example beeswax or carnauba wax; solid hydrocarbons, for example paraffin or earth wax; fatty acids, for example stearic acid; certain cellulose derivatives, for example ethylcellulose or acetylcellulose; polymers or copolymers, such as polyalkenes, for example polyethylene, polyvinyl compounds, for example polyvinyl chloride or polyvinyl acetate, and vinyl chloride/vinyl acetate copolymers and copolymers withcrotonic acid, or polymers and copolymers of acrylates and methacrylates, for example copolymers of acrylic ester and methyl methacrylate.

The delivery of active substances which are not particularly soluble in the neutral medium in the intestine but are more soluble in the acidic region of the stomach can also be controlled in addition using substances which have functional carboxyl groups and dissolve in the neutral range, for example shellac, cellulose esters, for example cellulose acetate phthalate or hydroxypropylmethylcellulose phthalate, or hemiesters of maleic anhydride copolymers.

Apart from the ancillary substances mentioned; the compositions according to the present invention may additionally contain bulking agents, disintegrants, binders and lubricants, and excipients which have no decisive effect on the delivery of active substances. Examples are, inter alia, bentonite (alumina silica hydrate), silica, cellulose (normally microcrystalline cellulose) or cellulose derivatives, for example methylcellulose, sodium carboxymethylcellulose, sugars such as lactose, starches, for example maize starch or derivatives thereof, for example sodium carboxymethyl-starch, starch paste, phosphoric acid salts, for example di- or tricalcium phosphate, gelatin, stearic acid or suitable salts thereof, for example magnesium stearate or calcium stearate, talc, colloidal silica and similar ancillary substances.

The carrier material loaded with active substances and ancillary substances and compressed is expediently provided with a coating. The simplest case comprises capsules into which the carrier material containing the active substance is introduced.

Coating with a coating material can likewise take place by conventional methods. The coating layer or protective layer can, for example, be sprayed on in a rotating pan or a fluidized bed reactor. After drying, the compositions according to the invention are ready for packing and despatch.

The compositions according to the invention are primarily designed for introduction into the body in the form of capsules, tablets, coated tablets, suppositories or other conventional solid forms. The specific nature of the carrier material employed results in it spreading on contact with fluid in the stomach or intestine or other body fluids and thereby the active substances which are present in the swelling foam-like structure are released after a delay and gently in accordance with the areas available as a consequence of the large volume. The swelling of the carrier material to a large volume ensures that the composition according to the invention is not deposited in folds of the wall of the stomach or intestine. It is thus no longer possible for local irritation to take place as a result of excessive concentrations of the active substance occurring in places. On the contrary, the resulting size of the carrier material ensures that the active substance is distributed over a large area, and thus gently, in the gastrointestinal tract, or other body cavities.

BRIEF DESCRIPTION OF THE DRAWINGS

The invention is explained in detail hereinafter with reference to the only FIGURE showing the carrier material in the compressed and swelled states.

DESCRIPTION OF THE PREFERRED EMBODIMENT

The pressed block 1, which may have various shapes, is initially produced. This preferably takes place according to the invention by pressing the carrier material. The pressed carrier material is subsequently cut to be suitable for administration. In the example according to the invention, this results in the depicted brick-shaped element 1. However, other shapes are also, of course, included within the scope of the invention.

Under the influence of fluid in the stomach or in the intestine, the large-volume element 2 is formed. The active substance release areas 3 are formed and are very much larger than the areas known from the state of the art. The active substance release areas 3 make it possible for active substances to be released considerably better, and thus more gently for the walls of the stomach and intestine, by comparison with conventional forms.

The active substance release areas 3 preferably have according to the invention a size of 15 to 25 $cm^2$. By contrast, the sizes of the active substance release areas in the state of the art hitherto are 0.5 to 1.5 $cm^2$. Accordingly, considerably better and gentler release of the active substance is achieved by the larger areas 3 according to the invention. The active substance 4, which is embedded in the foam carrier material is released in particular continuously and with some hours' delay. It is not possible with the considerably smaller active substance release areas in the state of the art to achieve even approximately the same effect.

I claim:

1. A composition for a delayed and gentle release of active substances in the human body after oral administration, the composition comprising a carrier material, which is insoluble in gastrointestinal fluids, and active substances, wherein the carrier material is comprised of proteins and the carrier material has a compressed sponge-like structure, wherein the sponge-like structure contains the active substances, and wherein the compressed sponge-like substance is configured to swell in the gastrointestinal fluids to a multiple of a volume of the compressed sponge-like structure and to continuously release with time delay the active substances via the large-surface area of the swelled sponge-like structure.

2. The composition according to claim 1, wherein the compressed sponge-like structure comprises a coating of a material which is soluble in water and in gastrointestinal fluids or body fluids.

3. The composition according to claim 1, wherein the active substances are added to the carrier material before, during or after the sponge-like structure is made of the carrier material.

4. The composition according to claim 1, wherein the carrier material is comprised of viscous sponges compressed to a compressed sponge-like structure, wherein the compressed sponge-like structure swells to a multiple of the volume of the compressed sponge-like structure in water or gastrointestinal fluids.

5. The composition according to claim 1, wherein the compressed sponge-like structure has a volume of not more than 2 $cm^3$.

6. The composition according to claim 4, wherein the compressed sponge-like structure swells 2 to 10 times its volume in water, in gastrointestinal fluids or body fluids.

7. The composition according to claim 4, wherein the compressed sponge-like structure swells 4 to 8 times its volume in water and in gastrointestinal fluids.

8. The composition according to claim 1, wherein the carrier material is comprised of natural polymers, semisynthetic polymers or synthetic polymers.

9. The composition according to claim 1, wherein the carrier material is comprised of linearly colloidal polymers.

10. The composition according to claim 9, wherein the carrier material is comprised of polymers with a fibrous structure.

11. The composition according to claim 10, wherein the carrier material is comprised of scleroproteins.

12. The composition according to claim 11, wherein the scleroproteins are collagens.

13. The composition according to claim 1, further containing ancillary substances.

* * * * *